United States Patent [19]

Mukunoki et al.

[11] 4,278,757
[45] Jul. 14, 1981

[54] SILVER HALIDE PHOTOGRAPHIC LIGHT-SENSITIVE MATERIAL

[75] Inventors: Yasuo Mukunoki; Masakazu Yoneyama; Jiro Yamaguchi; Hideki Naito; Jun Sasaki, all of Minami-ashigara, Japan

[73] Assignee: Fuji Photo Film Co., Ltd., Minami-ashigara, Japan

[21] Appl. No.: 65,496

[22] Filed: Aug. 10, 1979

[30] Foreign Application Priority Data

Aug. 10, 1978 [JP] Japan .................................. 53-97575

[51] Int. Cl.³ .......................... G03C 1/40; G03C 1/10; G03C 1/84; G03C 1/68
[52] U.S. Cl. ..................................... 430/512; 430/222; 430/517; 430/546; 430/559; 430/564; 430/566; 430/621; 430/631
[58] Field of Search ................ 430/222, 241, 546, 631, 430/512, 517, 559, 566, 621, 564

[56] References Cited

U.S. PATENT DOCUMENTS

| | | | |
|---|---|---|---|
| 2,322,027 | 6/1943 | Jelley et al. | 430/546 |
| 2,801,171 | 7/1957 | Fierke et al. | 430/546 |
| 2,949,360 | 8/1960 | Julian | 430/546 |

*Primary Examiner*—Richard L. Schilling
*Attorney, Agent, or Firm*—Sughrue, Rothwell, Mion, Zinn and Macpeak

[57] ABSTRACT

A silver halide photographic light-sensitive material having a hydrophilic organic colloid layer containing a dispersion of a substantially water-insoluble photographic additive dissolved in a phosphoric acid ester represented by the following general formula (I):

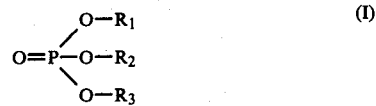

wherein $R_1$ represents a saturated alicyclic group; and $R_2$ and $R_3$, which may be the same or different, each represents a saturated alicyclic group, an alkyl group or an aryl group.

19 Claims, No Drawings

SILVER HALIDE PHOTOGRAPHIC LIGHT-SENSITIVE MATERIAL

BACKGROUND OF THE INVENTION

1. Field of the Invention

The present invention relates to a silver halide photographic light-sensitive material and, more particularly, to a silver halide photographic light-sensitive material containing a substantially water-insoluble photographic additive dispersed in a hydrophilic organic colloid layer using a specific phosphoric acid ester having a cycloalkyl group.

2. Description of the Prior Art

Conventionally, a substantially water-insoluble photographic additive, for example, an oil-soluble coupler, an antioxidant for preventing color stain or color contamination, a color fading preventing agent (such as an alkylhydroquinone, an alkylphenol, a chroman, a cumarone, etc.), a hardening agent, an oil-soluble filter dye, an oil-soluble ultraviolet absorbing agent, a DIR compound (such as a DIR hydroquinone, a non-color forming DIR compound, etc.), a developing agent, a dye developing agent, a DRR compound, a DDR coupler, and the like is dissolved in an appropriate organic solvent having a high boiling point, dispersed in an aqueous solution of a hydrophilic organic colloid, particularly gelatin, in the presence of a surface active agent and the resulting mixture is incorporated in a hydrophilic organic colloid layer, for example, a light-sensitive emulsion layer, a filter layer, a backing layer, an antihalation layer, an intermediate layer, a protective layer, and the like.

These high boiling point organic solvents are such that dispersion capability for substantially water-insoluble photographic additives, affinity to a gelatin layer, influence on the stability of the color image formed, chemical stability in photographic light-sensitive materials, influence on the photographic properties, and the like are good.

As high boiling point organic solvents for dispersion, those described, for example, in U.S. Pat. Nos. 2,322,027, 3,676,137 and 3,779,765, German Pat. No. 1,152,610, British Pat. No. 1,272,561, Japanese Patent Application (OPI) No. 1520/1978, etc. are known. Of these compounds, phthalic acid esters, triphenyl phosphoric acid esters and straight chain or branched chain-alkyl phosphoric acid esters are particularly useful as relatively preferred high boiling point organic solvents.

However, these high boiling point organic solvents do not always fulfill all requirements such as dispersion capability for substantially water-insoluble photographic additives, affinity to an organic hydrophilic colloid layer, influence on the photographic properties, chemical stability in photographic light-sensitive materials, and the like.

SUMMARY OF THE INVENTION

A first object of the present invention is to provide a photographic light-sensitive material containing a photographic additive dispersed therein using a high boiling point organic solvent which has a good dispersion capability and a good dispersion stability in a hydrophilic organic colloid.

A second object of the present invention is to provide a photographic light-sensitive material that is produced using a high boiling point organic solvent which does not adversely affect the photographic properties, such as fog, sensitivity, maximum image density, etc.

A third object of the present invention is to provide a color photographic light-sensitive material the light-fastness of which is improved.

A fourth object of the present invention is to provide a color photographic light-sensitive material in which the occurrence of stain due to humidity and heat can be prevented.

These and other objects will become apparent from the following description of the invention wherein a substantially water-insoluble photographic additive is dissolved in a phosphoric acid ester represented by the following formula (I):

wherein $R_1$ represents a saturated alicyclic group; and $R_2$ and $R_3$, which may be the same or different, each represents a saturated alicyclic group, an alkyl group or an aryl group, and the solution is dispersed into a hydrophilic organic colloid layer of a silver halide photographic light-sensitive material.

DETAILED DESCRIPTION OF THE INVENTION

In the above general formula, $R_1$ represents a substituted or unsubstituted saturated alicyclic group having 5 or more carbon atoms, preferably having up to 12 carbon atoms. Examples of the substituents include a straight, branched or cyclic alkyl group, preferably having 1 to 18 carbon atoms; a mono or bicyclic aryl group, preferably having 6 to 20 carbon atoms; a straight, branched or cyclic alkoxy group, preferably having 1 to 12 carbon atoms which may be further substituted with a alkoxy group having 1 to 18 carbon atoms; a cycloalkyl group, preferably having 6 to 12 carbon atoms; an alkoxyalkyl group, which may be straight, branched or cyclic, preferably having 2 to 18 carbon atoms; an acyloxy group, preferably having 2 to 20 carbon atoms; a halogen atom (e.g. F, Cl, Br, I), etc.

$R_2$ and $R_3$ each preferably represents a substituted or unsubstituted saturated alicyclic group having 5 or more carbon atoms (preferably up to 6 carbon atoms) where the substituents are defined as for $R_1$ above; a substituted or unsubstituted alkyl group having 1 to 30 carbon atoms which may be straight, branched or cyclic, with suitable substituents being a straight, branched or cyclic alkoxy group preferably having 1 to 18 carbon atoms, a halogen atom (e.g. F, Cl, Br, I), a mono or bicyclic aryl group preferably having 6 to 20 carbon atoms, an acyloxy group preferably having 2 to 20 carbon atoms, a mono or bicyclic aryloxy group, preferably having 6 to 20 carbon atoms, etc.; or a substituted or unsubstituted aryl group, which may be mono or bicyclic, preferably having 6 to 24 carbon atoms with suitable substituents being an alkyl group, an alkoxy group or a halogen atom which are the same as defined for the above substituents of alkyl group. The carbon atom range for the total number of carbon atoms in $R_1+R_2+R_3$ is preferably 12 to 50, more preferably 14 to 36.

From the standpoint of the ability of the phosphoric acid ester to disperse a substantially water-insoluble photographic additive in a hydrophilic organic colloid, low cost and being easily synthesized or commercially available, the phosphoric acid ester of the formula (I) in which $R_1$, $R_2$ and $R_3$ represent a substituted or unsubstituted saturated alicyclic group is preferred. the phosphoric acid ester wherein each of $R_1$, $R_2$ and $R_3$ represents an unsubstituted or alkyl-substituted saturated alicyclic group is more preferred and in particular phosphoric acid esters wherein each of $R_1$, $R_2$ and $R_3$ represents an unsubstituted or $C_1$-$C_4$ alkyl-substituted saturated alicyclic group. The phosphoric acid ester wherein each of $R_1$, $R_2$ and $R_3$ represents an unsubstituted saturated alicyclic group and in particular a cyclohexyl group is most preferred. Of the saturated alicyclic groups above, saturated alicyclic groups having 5 to 12 carbon atoms such as a cyclopentyl group, a cyclohexyl group, a cycloheptyl group, a cyclododecyl group, etc. are preferred and, a cyclohexyl group is particularly preferred.

Specific examples of the phosphoric acid esters represented by the general formula (I) which can be used in the present invention are shown below. However, the present invention is not to be construed as being limited to these examples.

Compound (1)

Compound (2)

Compound (3)

Compound (4)

Compound (5)

Compound (6)

Compound (7)

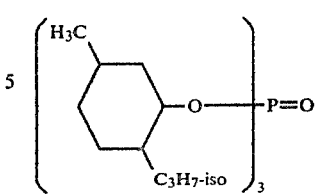
Compound (8)

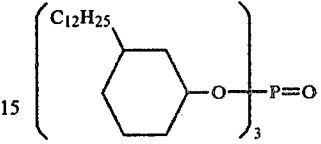
Compound (9)

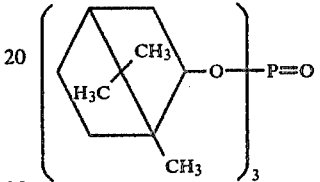
Compound (10)

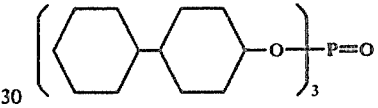
Compound (11)

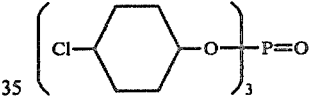
Compound (12)

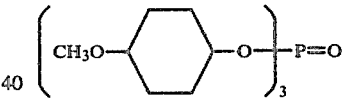
Compound (13)

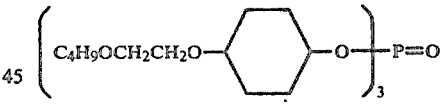
Compound (14)

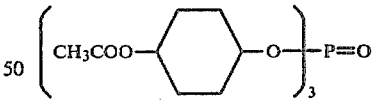
Compound (15)

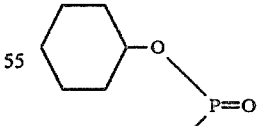
Compound (16)

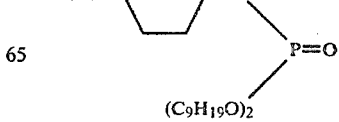
Compound (17)

Compound (18)

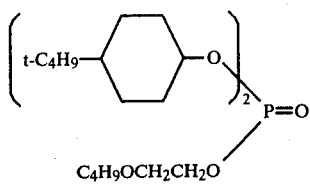

Compound (19)

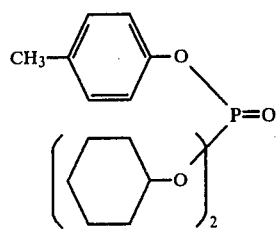

The phosphoric acid ester represented by the general formula (I) which can be used in the present invention has a boiling point above about 200° C. at normal pressure (1 atmosphere pressure).

The phosphoric acid esters represented by the general formula (I) which can be used in the present invention can generally be obtained by reacting a phosphorous oxychloride with a cyclic saturated alcohol in the presence of a catalyst (for example, a base such as pyridine, triethylamine, etc., titanium tetrachloride, etc.). General synthesis methods are described, for example, in U.S. Pat. No. 3,209,021, Japanese Patent Publication No. 28429/1973, U.S. Pat. Nos. 1,799,349, and 2,426,691, *Organophosphorus Compounds*, John Wiley & Sons, Inc., New York, pages 266 and 288 (1950), etc. Specific examples of the Synthesis of phosphoric acid esters represented by the general formula (I) are shown below.

SYNTHESIS EXAMPLE 1

Synthesis of Compound (1): Tricyclopentyl Phosphate

To a solution of 86.1 g (1 mol) of cyclopentanol, 79.1 g (1 mol) of pyridine and 150 ml of toluene, 46.0 g (0.3 mol) of phosphorous oxychloride was added dropwise with stirring for 30 minutes while maintaining the reaction temperature below 20° C. The mixture was gradually heated and stirred for 3 hours at 70° C. After cooling, the reaction solution was washed with water, an aqueous solution of sodium hydroxide and water, in this order and dried with anhydrous sodium sulfate. After filtering the mixture, the filtrate was concentrated under reduced pressure and the crude tricyclopentyl phosphate was purified by column chromatography to obtain 52.0 g of the desired compound (1). $\eta_D^{25}$ 1.4720

In the purification by column chlomatography, 800 g of Silicagel 60 manufactured by Merck Co. was used as the carrier and hexane-ether (9:1 in volume ratio) and hexane-ether (7:3 in volume ratio) were used as the solvents.

SYNTHESIS EXAMPLE 2

Synthesis of Compound (3): Tricycloheptyl Phosphate

To a solution of 50 g (0.44 mol) of cycloheptanol and 34.7 g (0.44 mol) of pyridine, 22.4 g (0.146 mol) of phosphorous oxychloride was added dropwise with stirring for 20 minutes. After the completion of the addition, the mixture was further stirred at 60° C. for 2 hours to complete the reaction. 100 ml of toluene was added to the reaction solution and the product was purified in the same manner as described in Synthesis Example 1 to obtain 25.8 g of the desired tricycloheptyl phosphate.

SYNTHESIS EXAMPLE 3

Synthesis of Compound (2): Tricyclohexyl Phosphate

To a solution of 992 g (9.9 mol) of cyclohexanol and 744 g (9.4 mol) of pyridine, 460 g (3 mol) of phosphorous oxychloride was added dropwise with stirring for 2 hours while maintaining the inner temperature at 10° to 25° C. After the completion of the addition, the mixture was stirred at 70° C. for 4 hours in order to complete the reaction. After the completion of the reaction, 1.5 l of toluene was added to reaction mixture. The mixture was washed with diluted hydrochloric acid, water, a diluted sodium carbonate aqueous solution and water, in this order and dried with anhydrous sodium sulfate. After filtering the mixture, the crude tricyclohexyl phosphate thus obtained was distilled in high vacuum. Boiling Point: 90° to 100° C./0.01 to 0.03 mmHg. Yield: 785 g (76%).

SYNTHESIS EXAMPLE 4

Synthesis of Compound (8): Tri(2-isopropyl-5-methylcyclohexyl) phosphate

To a solution of 234.4 g (1.5 mol) of menthol, 118.7 g (1.5 mol) of pyridine and 300 ml of chloroform, 76.7 g (0.5 mol) of phosphorous oxychloride was added dropwise with stirring for 30 minutes while maintaining the inner temperature at 10° to 25° C. After further stirring at 30° to 50° C. for 2 hours, the reaction mixture was washed with water, a diluted sodium hydroxide aqueous solution and water, in this order and dried with anhydrous sodium sulfate. After filtration, the filtrate was concentrated under reduced pressure and treated in the same manner as described in Synthesis Example 1 to obtain desired compound (10). Silicagel 60 used in the treatment was 2 Kg. Yield: 187.1 g (73%).

SYNTHESIS EXAMPLE 5

Synthesis of Compound (19): Dicyclohexyl Mono-p-cresyl phosphate 108 g (1 mol) of p-cresol and 79.1 g (1 mol) of pyridine were added dropwise to 300 ml of chloroform solution containing 153.4 g (1 mol) of phosphorous oxychloride and the mixture was stirred at 50° C. for 2 hours. To the solution, 200 g (2 mol) of cyclohexanol and 158 g (2 mol) of pyridine were added dropwise while maintaining the inner temperature at 10° to 30° C. The mixture was reacted at room temperature for 2 hours and then at 70° C. for 2 hours. After cooling the reaction solution, it was washed with water, a saturated sodium hydrogen carbonate aqueous solution and water, in this order and dried with anhydrous sodium sulfate. After filtration, chloroform was removed under reduced pressure and the residual oil was distilled in high vacuum. Yield: 108.2 g. Boiling Point: 98° to 105° C./0.02 to 0.04 mmHg.

The phosphoric acid esters represented by the general formula (I) according to the present invention can be used individually as a high boiling point organic solvent for dissolving a substantially water-insoluble photographic additive or the esters can be used in combination with other known high boiling point organic solvents.

The amount of the phosphoric acid ester represented by the general formula (I) which can be used ranges from about 0.05 to about 15 parts by weight, preferably from 0.1 to 6.parts by weight, per part by weight of the substantially water-insoluble photographic additive.

All compounds which have been dispersed in hydrophilic organic colloid layers using conventional high boiling point organic solvents can be advantageously employed as substantially water-insoluble photographic additives in the present invention.

Representative examples of substantially water-insoluble photographic additives are a photographic coupler, an antioxidant and a fading preventing agent capable of preventing color fog and fading of the color image formed, for example, an alkylhydroquinone, an alkylphenol, a chroman, a cumarone, etc., a hardening agent, a compound which selectively absorbs visible light or ultraviolet light such as an oil-soluble filter dye or an oil-soluble ultraviolet absorbing agent, a fluorescent brightening agent, a DIR compound, for example, a DIR hydroquinone, a DIR coupling compound, etc., a developing agent, a DDR coupler, a DRR compound, a dye developing agent, and the like. Of the above examples of substantially water-insoluble additives, a photographic coupler, an ultraviolet ray absorbing agent, a fade preventing agent and a DRR compound are particularly effectively dispersed in a hydrophilic organic colloid by the phosphoric acid ester of the present invention.

The excellent effects of the phosphoric acid ester according to the present invention will be understood from the Examples described hereinafter.

The photographic couplers which can be used in the present invention include compounds which are capable of forming a dye upon oxidative coupling with an aromatic primary amine developing agent, for example, a phenylenediamine derivative, an aminophenol derivative, etc. For instance, examples of such couplers are 5-pyrazolone couplers, pyrazolobenzimidazole couplers, cyanoacetyl cumarone couplers, open chain acylacetonitrile couplers as magenta couplers, acylacetamide couplers such as benzoylacetanilide and pivaloylacetanilide as yellow couplers, naphthol couplers, phenol couplers as cyan couplers, and the like.

Suitable magenta couplers which can be used in the present invention include those described, for example, in U.S. Pat. Nos. 2,600,788, 3,558,319, 3,935,015, 3,933,500, 3,926,631, 3,061,432, 4,012,259, 3,476,560, 3,227,550, 3,252,924, 3,311,476, and 3,419,391, British Pat. No. 1,293,640, German Patent Application (OLS) Nos. 2,015,867, 2,418,959, 2,414,832, 2,424,467, 2,510,538 and 2,526,112, Japanese Patent Application (OPI) Nos. 110665/1974 and 117464/1974, etc.

Suitable development inhibitor releasing (DIR) couplers which can be used in tne present invention include those described, for example, in U.S. Pat. Nos. 3,148,062, 3,227,554, 3,615,506, 3,701,783, 3,790,384, 3,617,291, 3,632,345, 3,933,500, etc.

Suitable yellow couplers which can be used in the present invention include those described, for example, in U.S. Pat. Nos. 3,227,550, 3,253,924, 3,277,155, 3,265,506, 3,408,194 and 3,415,652, French Pat. No. 1,411,384, British Pat. Nos. 944,490, 1,040,710 and 1,118,028, German Patent Application (OLS) Nos. 2,057,941, 2,163,812, 2,213,461 and 2,219,971, etc.

Suitable cyan couplers which can be used in the present invention include those described, for example, in U.S. Pat. Nos. 2,423,730, 3,227,550 and 3,311,476, British Pat. Nos. 1,084,480 and 1,165,563, U.S. Pat. Nos. 2,983,608, 3,005,712 and 3,034,892, British Pat. Nos. 936,621, 1,269,073, 586,211 and 627,814, French Pat. Nos. 980,372, 1,091,903, 1,257,887, 1,398,308 and 2,015,649, etc.

Non-color forming DIR compounds which can be used in the present invention includes those described, for example, in U.S. Pat. Nos. 3,632,345 and 3,379,529, German Patent Application (OLS) Nos. 2,610,546, 2,610,548 and 2,527,652, Japanese Patent Application (OPI) No. 72433/1976, etc.

Photographic additives suitable for use in a diffusion transfer photographic material which can be used in the present invention include, for example, diffusible dye releasing type redox compounds (DRR compounds), diffusible dye releasing type couplers (DDR couplers), dye developing agents, amidrazone compounds which release a diffusible dye upon reaction with an oxidation product of a developing agent, and the like.

In more detail, the diffusible dye releasing type redox compounds (DRR compounds) as described, for example, in Japanese Patent Application (OPI) Nos. 33826/1973, 115528/1975, 114424/1974, 113624/1976, 126331/1974, 126332/1974 and 114930/1976, U.S. Pat. Nos. 3,932,380 and 3,931,144, German Patent Application (OLS) No. 2,613,005, etc., the diffusible dye releasing couplers which release a diffusible dye upon reaction with a color developing agent (DDR couplers) as described, for example, in British Pat. Nos. 840,731, 904,364 and 1,038,331, U.S. Pat. Nos. 2,756,142, 3,227,550, 3,227,551, 3,227,554 and 3,765,886, U.S. Defensive Publication No. T-900,029, Japanese Patent Application (OPI) Nos. 123022/1974 and 133021/1976, German Patent Application (OLS) No. 2,630,999, etc., the amidrazone compounds which release a diffusible dye upon reaction with an oxidation product of a developing agent as described, for example, in Japanese Patent Publication No. 39165/1973, Japanese Patent Application (OPI) Nos. 2327/1972 and 64436/1974, etc., the dye developing agents as described, for example, in U.S. Pat. Nos. 3,953,211, 3,793,028, 3,999,991, 4,014,700, 2,983,606, 3,551,406, 3,563,739, 3,597,200, 3,674,478, 3,320,063, 3,230,082, 3,307,947, 3,579,334, 3,299,041, 2,983,605, 3,994,731, 2,992,106, 3,047,386, 3,076,808, 3,076,820, 3,077,402, 3,126,280, 3,131,061, 3,134,762, 3,134,765, 3,135,604, 3,136,605, 3,135,606, 3,135,734, 3,141,772, 3,142,565, 3,173,906, 3,183,090, 3,246,985, 3,230,086, 3,309,199, 3,230,083, 3,239,339, 3,347,672, 3,347,673, 3,245,790 and 3,230,082, German Patent Application (OLS) No. 2,458,212, Japanese Patent Application (OPI) Nos. 42536/1976, 117456/1974 and 161525/1975, etc., can be employed.

Antioxidants which can be used in the present invention include phenol or hydroquinone derivatives or precursors thereof having an aliphatic group of 8 or more carbon atoms such as those compounds described, for example, in U.S. Pat. Nos. 2,336,327, 2,728,659 and 2,835,579 and Japanese Patent Application (OPI) No. 2128/1971.

Further, the compounds described in German Pat. No. 1,547,684, German Patent Application (OLS) No. 2,146,668 and Belgian Pat. No. 777,487 are particularly suitable in this invention as an antioxidant for color images.

Filter dyes which can be used in the present invention include oleophilic oxanol dyes, benzotriazole type ultraviolet absorbing agents and benzophenone type ultraviolet absorbing agents such as those compounds described, for example, in Japanese Patent Publication Nos. 21687/1967 and 5496/1973, Japanese Patent Application (OPI) Nos. 1026/1972 and 2784/1971 and British Pat. No. 1,293,982, etc.

The phosphoric acid ester according to the present invention can also be used advantageously to disperse these substantially water-insoluble photographic additives and incorporate the additives into a hydrophilic organic colloid layer. In particular, the phosphoric acid ester can be advantageously used for dispersing a photographic coupler and incorporating the coupler into a light-sensitive silver halide emulsion layer. That is, in photographic light-sensitive materials in which a photographic coupler is dispersed and incorporated using a phthalic acid ester type compound such as dibutyl phthalate, etc., a triphenyl phosphoric acid ester type compound such as tricresyl phosphate, etc., or a straight chain or branched chain-alkyl phosphoric acid ester type compound such as dioctyl butyl phosphate, etc., the stability of the dispersion and the stability of the color image formed by exposure and development processing is not sufficient. On the contrary, however, the stability of the dispersion and the stability of the color image formed in remarkably improved by using the phosphoric acid ester according to the present invention.

In this respect, the phosphoric acid ester according to the present invention provides extraordinary effects and in particular, with respect to the stability of the coupler dispersion.

The phosphoric acid esters according to the present invention can be used in combination with a substantially water-insoluble low boiling point auxiliary solvent (preferably, a substantially water-insoluble solvent having a boiling point up to 150° C., most preferably up to 120° C., for example lower alkyl acetates, e.g., methyl acetate, ethyl acetate, butyl acetate, and the like) or a water-soluble organic auxiliary solvent (e.g., an organic solvent of which at least two parts by volume can be dissolved in 100 parts by volume of water such as methyl isobutyl ketone, β-ethoxy ethyl acetate, methyl carbitol, methyl Cellosolve, dipropylene glycol, dimethylformamide, dioxane or the like). These low boiling point auxiliary solvents are described, for example, in U.S. Pat. Nos. 2,801,170, 2,801,171, 2,949,360, and 2,835,579. These auxiliary solvents can be removed by washing with water as described in U.S. Pat. Nos. 2,801,171, 2,949,360 and 3,396,027 or can be removed by vaporization as described in U.S. Pat. Nos. 2,322,027 and 2,801,171 and German Patent Application (OLS) No. 2,045,464. A suitable volume ration for the auxiliary solvent to the phosphoric acid ester according to the present invention is about 0.1 to 30 and particularly 0.2 to 10.

The photographic additives such as couplers, antioxidants, ultraviolet absorbing agents, filter dyes, and the like, individually or as a mixture of two or more thereof, can be dissolved in the phosphoric acid ester of the present invention and the solution is dispersed in an aqueous solution of a hydrophilic organic colloid, particularly gelatin. In such a case, the use of one or more of the phosphoric acid esters in combination with an auxiliary solvent is particularly preferred. Useful dispersion procedures are described, for example, in U.S. Pat. Nos. 2,304,939, 2,322,027, 2,801,170, 2,801,171 and 2,949,360.

The photographic additives can be dissolved in the phosphoric acid ester according to the present invention dispersed in an aqueous solution of a hydrophilic colloid together with a polymer latex (e.g., polymethylacrylate latex, polyethylmethacrylate latex, etc.) and incorporated into a hydrophilic organic colloid layer. Such dispersing methods are described, for example, in Japanese Patent Application (OPI) Nos. 74538/1974 and 59943/1976.

An anionic surface active agent (such as a sodium alkylbenzenesulfonate, sodium dioctylsulfosuccinate, sodium dodecyl sulfate, a sodium alkylnaphthalene sulfonate, a Fisher type coupler, and the like), an amphoteric surface active agent (such as N-tetradecyl-N,N-dipolyethylene-α-betaine, and the like), and a nonionic surface active agent (such as sorbitan monolaurate, and the like) can be used as an auxiliary dispersion agent.

The hydrophilic organic colloid layer according to the present invention can be any photographic layer containing a hydrophilic organic colloid as a binder. Examples of suitable hydrophilic organic colloids are gelatin, which is most commonly used, cellulose derivatives, sodium alginate, hydrophilic synthetic polymers (such as polyvinyl alcohol, polyvinyl pyrrolidone, polystyrene sulfonic acid, copolymers of styrene sulfonic acid, copolymers of maleic acid, copolymers of acrylic acid, copolymers of methacrylic acid, copolymers of itaconic acid, and the like), modified gelatins (such as phthalated gelatin, and the like), and the like. The above-described hydrophilic organic colloids other than gelatin can be used individually or as a mixture of two or more of such colloids, but they are conventionally used together with gelatin. The hydrophilic organic colloid layer can optionally contain a polymer latex (such as a polymethyl methacrylate latex, a polyethyl acrylate latex, and the like) to improve the physical properties of the photographic layer.

Representative examples of hydrophilic organic colloid layers include silver halide photographic light-sensitive layers and non-light-sensitive photographic auxiliary layers (such as a protective layer, an intermediate layer, a filter layer, an irradiation preventing layer, an antihalation layer, a backing layer, a development contamination preventing layer, a barrier layer, and the like).

The silver halide emulsions which can be used in the present invention are photographic emulsions containing a silver halide such as silver bromide, silver iodide, silver chloride or mixtures thereof, e.g., silver chlorobromide, silver iodobromide, and silver chloroiodobromide.

Furthermore, the color photographic light-sensitive material according to the present invention can contain an intermediate silver to prevent color mixing, a filter layer, a mordant dyed layer, a colored layer containing a hydrophobic dye, etc., in addition to the light-sensitive silver halide emulsion layer.

The light-sensitive silver halide emulsion used in the present invention can be coated on various kinds of supports. For example, a cellulose acetate film, a polyethylene terephthalate film, a polyethylene film, a polypropylene film, a glass plate, baryta paper, a synthetic resin laminated paper, a synthetic paper, etc., can be used.

For the photographic light-sensitive material of the present invention, a developer solution capable of reducing the exposed silver halide grains to silver can be used in processing for forming images. In black and white development, a developer solution containing, as a developing agent, a polyhydroxy benzene, an N- alkylaminophenol, a 1-phenyl-3-pyrazolidone, or a mixture thereof can be used. Examples of suitable compounds include hydroquinone, pyrogallol, N-methylaminophenol, 1-phenyl-3-pyrazolidone, 1-phenyl-4,4-dimethyl-3-pyrazolidone and the like. In color development, a developer solution containing, as a developing agent, a para-phenylenediamine derivative such as 4-amino-N,N-diethylaniline, 4,-amino-3-methyl-N-methyl-N-(β-methylsulfonamidoethyl)aniline, 4-amino-3-methyl-N-ethyl-N-(β-hydroxyethyl)aniline, 4-hydroxyaniline, 4-hydroxy-2,6-dibromoaniline and the like, can be used.

The photographic light-sensitive material of the present invention can be processed at conventional processing temperatures, e.g., about 20° to 30° C., and it is also possible to process the photographic material at a higher temperature, e.g., about 30° to 60° C. or higher.

Preferred procedures for processing the color light-sensitive material according to the present invention are described, for example, in Japanese Patent Publication No. 35749/1970, U.S. Pat. No. 3,695,883, German Patent Application (OLS) Nos. 2,211,815 and 2,215,382, H. Gordon, *The British Journal of Photography*, page 558 (Nov. 15, 1954), ibid., page 440 (Sept. 9, 1955), ibid., page 2 (Jan. 6, 1956), S. Horwitz, *The British Journal of Photography*, page 212 (Apr. 22, 1960), E. Gehret, *The British Journal of Photography*, page 122 (Mar. 4, 1960), ibid., page 396 (May 7, 1965), J. Meech, *The British Journal of Photography*, page 182 (Apr. 3, 1959), German Patent Application (OLS) No. 2,238,051, etc.

The color photographic light-sensitive material wherein the phosphoric acid ester according to the present invention is used has an advantage in that the silver image obtained or reduced silver can be easily bleached.

The technique according to the present invention can be applied to a color negative light-sensitive material, a color reversal light-sensitive material, a color direct-positive type light-sensitive material, a transparent color positive light-sensitive material, a color paper light-sensitive material, a DTR process type light-sensitive material for instant photography, a color X-ray light-sensitive material, a monochromatic light-sensitive material for industrial use, etc. Further, where a developing agent, an antioxidant or a filter dye is used, the technique according to the present invention can be applied to a black and white light-sensitive material or an unconventional light-sensitive material.

The color light-sensitive material of the present invention can also be a color photographic light-sensitive material in which a smaller amount of silver halide is used as is described in German Patent Application (OLS) No. 2,357,964, etc. For example, such a color photographic light-sensitive material containing a small amount of silver halide includes from several tenths to one hundredth (for example, about 65 to 375 mg/m² of silver halide per layer) as much silver halide as that in a conventional color photographic light-sensitive material for obtaining the same density.

The color photographic light-sensitive materials containing silver halide in such a small amount to which the present invention is applicable can be subjected to a processing method in which the developed silver formed by color development is halogenation-bleached and again color developed in order to increase the amount of dye formed, as described, for example, in U.S. Pat. Nos. 2,623,822 and 2,814,565, etc., a processing method including color intensification using a peroxide as described in U.S. Pat. Nos. 3,674,490 and 3,761,265, German Patent Application (OLS) No. 2,056,360, Japanese Patent Application (OPI) Nos. 6338/1972 and 10538/1972, etc., or using a cobalt complex salt as described in German Patent Application (OLS) No. 2,226,770, Japanese Patent Application (OPI) Nos. 9728/1973 and 9729/1973, etc.

The present invention is explained in greater detail below by reference to the following examples. However, the invention is not to be interpreted as being limited to these examples.

EXAMPLE 1

8 g of a ultraviolet absorbing agent having the following formula (I):

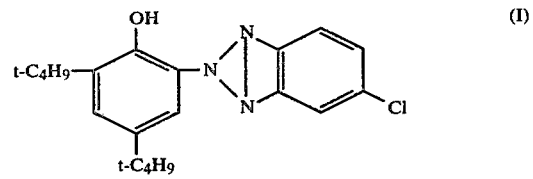

was added to a mixture of 8 g of the compound shown in Table 1 below and 25 cc of ethyl acetate and the mixture was heated at 70° C. to dissolve. The solution thus prepared was added to 100 cc of a 10% aqueous gelatin solution containing 0.5 g of sodium dodecylbenzenesulfonate and the mixture was stirred. Then the mixture was passed five times through a colloidal mill to prepare a dispersion.

The dispersion was maintained at 40° C. for 24 hours and filtered using a filter paper, i.e., Toyo Filter Paper No. 5B. The results, e.g., the amount of crystal deposited and the capability of filtration are shown in Table 1.

TABLE 1

| Sample | Compound | Amount of crystals deposited (mg) |
|---|---|---|
| a (Present Invention) | Compound (2) | 15 |
| b (Comparison) | Dibutyl phthalate | stuffed* |
| c (Comparison) | Tricresyl phosphate | 183 |

*the filter paper was stuffed meaning the amount of crystals deposited is very large and the dispersion is poor.

As is apparent from the results shown in Table 1 above, Sample a in which Compound (2) according to the present invention was used had a small amount of crystals deposited of ultraviolet absorbing agent (I) and was able to be filtered in comparison with Samples b and c for comparison. The results show that the compound according to the present invention is particularly excellent as a high boiling point organic compound for dispersion.

EXAMPLE 2

Same procedure as described in Example 1 was repeated except that 10 g of a yellow coupler, α-pivaloyl-α-(2,4-dioxo-5,5-dimethyl-3-oxazolidinyl)-2-chloro-5-[γ-(2,4-di-tert-amylphenoxy)butanamido]acetanilide [Coupler (II)] was added to a mixture of 15 g of the compound shown in Table 2 below and 20 ml of ethyl acetate and the amount of crystals deposited was measured. The results are shown in Table 2.

TABLE 2

| Sample | Compound | Amount of Crystals Deposited (mg) |
| --- | --- | --- |
| d (Present invention) | Compound (2) | 23 |
| e (Present invention) | Compound (7) | 37 |
| f (Comparison) | Tricresyl phosphate | stuffed* |
| g (Comparison) | Dioctyl butyl phosphate | stuffed* |

*See Example 1.

As is apparent from the results shown in Table 2 above, Samples d and e according to the present invention had a very small amount of crystals deposited of Yellow Coupler (II) and was able to be filtered in comparison with Samples f and g for comparison. The results show that the compounds according to the present invention are excellent as a high boiling point organic compound for comparison.

EXAMPLE 3

A solution prepared by heating at 70° C. a mixture of 27 g Yellow Coupler (III), α-pivalyl-α-(2,4-dioxo-5,5-dimethyl-3-oxazolidinyl-2-chloro-5-[α-(2,4-di-tert-amylphenoxy)butanamido]acetanilide, 27 g of Compound (2) according to the present invention and 50 ml of ethyl acetate was added to 300 ml of an aqueous solution containing 50 g of gelatin and 2.0 g of sodium dodecylbenzenesulfonate and the mixture was stirred. Then the mixture was passed five times through a preheated colloidal mill, whereby the couplers were finely dispersed together with the solvents.

All of the dispersion thus prepared was added to 1.0 kg of a photographic emulsion containing 54 g of silver iodobromide and 60 g of gelatin and 30 ml of a 5% acetone solution of triethylenephosphoramide, as a hardener, was added to the mixture. After adjusting the pH to 6.0, the mixture was coated on a cellulose triacetate film support in a dry thickness of 7.0 microns. This film was designated Sample A.

Films were prepared in the same manner as described above but using 27 g of Compounds (5), (6), (9) and (19) according to the present invention and a solvent mixture of 13.5 g of Compound (2) and 13.5 g of dioctyl butyl phosphate in place of Compound (2), respectively. These films were designated Samples B, C, D, E and F, respectively. For comparison, the same procedures as described above were repeated using the same amount of dioctyl butyl phosphate (DOBP) in place of Compound (2) to prepare a film. This film was designated Sample G.

These films were subjected to sensitometric stepwise exposure and then processed in the following manner.

| Color processing steps | | | |
| --- | --- | --- | --- |
| 1. | Color development | 30° C. | 4 minutes |
| 2. | Blixing | 30° C. | 2 minutes |
| 3. | Washing | 30° C. | 2 minutes |
| 4. | Stabilizing | 30° C. | 2 minutes |

The composition of each processing solution used is described below.

| Color Developer Solution | |
| --- | --- |
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (borate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfonamidoethyl)-amino-2-methylaniline Sesquisulfate | 8 g |
| Water to make | 1 l (pH 10.2) |

| Blixing Solution | |
| --- | --- |
| Ethylenediamine Tetraacetic Acid Ferric Salt | 45 g |
| Ammonium Thiocyanate | 10 g |
| Sodium Sulfite | 10 g |
| Ammonium Thiosulfate (60 wt% aq. soln.) | 100 ml |
| Sodium Ethylenediamine Tetraacetate | 5 g |
| Water to make | 1 l (pH 6.9) |

| Stabilizing Bath | |
| --- | --- |
| Tartaric Acid | 10 g |
| Zinc Sulfate | 10 g |
| Sodium Metaborate | 20 g |
| Water to make | 1 l |

The films thus-processed were subjected to light stability testing. The samples were set in a xenon fade testing device and exposed to light of $2.5 \times 10^6$ lux.hr for 8 days.

Then the percent decrease of the color density of the exposed sample was measured in comparison with that of the sample which had not been subjected to the light stability testing. The results of the present decrease of the color density in the color image at an initial density of 0.50 and 1.50 are shown in Table 3 below.

TABLE 3

| | | Percent Decrease in Color Density | |
| --- | --- | --- | --- |
| | | Initial Density | |
| Sample | Compound | 0.50(%) | 1.50(%) |
| A | (2) | 25 | 13 |
| B | (5) | 31 | 20 |
| C | (6) | 26 | 15 |
| D | (9) | 29 | 21 |
| E | (19) | 34 | 23 |
| F | (2) + DOBP | 46 | 32 |
| G (Comparison) | DOBP | 60 | 45 |

In the table DOBP indicates dioctyl butyl phosphate.

As is apparent from the results shown in Table 3 above, in Samples A, B, C, D, E and F wherein the compounds according to the present invention were used, the light fading of the color image was small and superior in comparison with Comparison Sample G.

EXAMPLE 4

Using a solution prepared by heating at 70° C. a mixture of 19.1 g of Cyan Coupler (VI), 2-[α-(2,4-di-tert-amylphenoxy)butanamido]-4,6-dichloro-5-methylphenol, 12.4 g of Compound (2) according to the present invention and 40 ml of ethyl acetate, the same procedure as described in Example 3 was repeated to prepare Sample H.

For comparison, Sample I was prepared using the same weight of dibutyl phthalate in place of Compound (2).

The processed samples were produced in the same manner as described in Example 3 and the fastness after storage in the dark at 100° C. for 1 week and the fastness after storage in the dark at 60° C. and 75% RH for 6 weeks were determined. The percent decrease in density (%) based on the initial density thus obtained is shown in Table 4 below.

TABLE 4

| Sample | 100° C. for 1 Week | | 60° C., 75% RH for 6 Weeks | |
|---|---|---|---|---|
| | $D_{0.5}(\%)$ | $D_{1.5}(\%)$ | $D_{0.5}(\%)$ | $D_{1.5}(\%)$ |
| H | 34 | 37 | 9 | 12 |
| I (Comparison) | 41 | 46 | 13 | 15 |

From the results shown above, it is apparent that color images having a good fastness to heat and humidity are formed when Compound (2) according to the present invention is used.

EXAMPLE 5

On a paper support with polyethylene layers laminated on both sides thereof were coated the following First Layer (as the lowermost layer) to the Sixth Layer (as the uppermost layer) to prepare a multilayer color light-sensitive material (Sample J). (In the following table, mg/m² represents the amount coated.)

| Sixth Layer (protective layer) | Gelatin | 1,500 mg/m² |
|---|---|---|
| Fifth Layer (red-sensitive layer) | Silver Chlorobromide Emulsion (Silverbromide: 50 mol %; 300 mg silver/m²) | |
| | Gelatin | 1,500 mg/m² |
| | Cyan Coupler*⁷ | 500 mg/m² |
| | Coupler Solvent*² | 250 mg/m² |
| Fourth Layer (UV-light absorbing layer) | Gelatin | 1,200 mg/m² |
| | UV Light-Absorbing Agent*³ | 1,000 mg/m² |
| | Solvent for UV Light-Absorbing Agent*² | 250 mg/m² |
| Third Layer (green-sensitive layer) | Silver Chlorobromide Emulsion (Silverbromide: 50 mol %; 450 mg silver/m²) | |
| | Gelatin | 1,500 mg/m² |
| | Magenta Coupler*⁴ | 400 mg/m² |
| | Coupler Solvent*⁵ | 200 mg/m² |
| Second Layer | Gelatin | 1,000 mg/m² |
| First Layer | Silver Chlorobromide Emulsion (Silverbromide: 80 mol %; 450 mg silver/m²) | |
| | Gelatin | 1,500 mg/m² |
| | Yellow Coupler*⁶ | 500 mg/m² |
| | Coupler Solvent*⁷ | 500 mg/m² |
| Support | Polyethylene Laminated Paper | |

*¹Cyan Coupler: 2-[α-(2,4-di-t-amylphenoxy)butanamido]-4,6-dichloro-5-methylphenol
*²Coupler Solvent: Di-n-butyl phthalate
*³UV Light-Absorbing Agent: 2-(2-Hydroxy-3-sec-butyl-5-t-butyl-phenyl)-benzotriazole
*⁴ Magenta Coupler: 1-(2,4,6-Trichlorophenyl)-3-(2-chloro-5-tetradecanamido)anilino-2-pyrazolin-5-one
*⁵Coupler Solvent: Tricresyl phosphate
*⁶Yellow Coupler: Yellow Coupler (III) (Same as in Example 3)
*⁷Coupler Solvent: Dioctylbutyl phosphate (DOBP)

Using Compound (2) according to the present invention in place of the coupler solvent in the First Layer of Sample J, Sample K was prepared. In Sample K, the weight ratio of the yellow coupler to the coupler solvent was 1:1 as in Sample J for comparison.

Each sample was exposed for ½ second to blue light, green light and red light through a continuous wedge, and then processed in the following manner.

| Step | Time | Temperature |
|---|---|---|
| Color Development | 3 min 30 sec | 33° C. |
| Blixing | 1 min 30 sec | " |
| Washing | 2 min | " |
| Drying | | |

The processing solutions used had the following composition.

| Color Developer Solution | |
|---|---|
| Benzyl Alcohol | 15 ml |
| Sodium Sulfite | 5 g |
| Potassium Bromide | 0.5 g |
| Hydroxylamine Sulfate | 2.0 g |
| Sodium Carbonate | 30.0 g |
| Sodium Nitrilotriacetate | 2.0 g |
| 4-Amino-3-methyl-N-(β-methanesulfonamido)-N-ethylaniline sesquisulfate | 5.0 g |
| Water to make | 1,000 ml (pH 10.1) |
| Blixing Solution | |
| Ammonium Thiosulfate | 105 g |
| Sodium Sulfite | 2 g |
| Disodium Ethylenediaminetetraacetate | 40 g |
| Sodium Carbonate (monohydrate) | 5 g |
| Water to make | 1,000 ml (pH 7.0) |

The samples thus processed were subjected to light stability testing using a xenon fade testing device ($2.0 \times 10^6$ lux-140 hr.). The color density of the image after 140 hours at an initial density of 1.5 and 0.5 was measured and the percent decrease in color density obtained is shown in Table 5 below.

TABLE 5

| | | Percent Decrease in Color Density Initial Density | |
|---|---|---|---|
| Sample | Compound | 0.5 (%) | 1.50 (%) |
| J (Comparison) | DOBP | 58 | 50 |
| K (Present invention) | (2) | 31 | 20 |

From the results shown above, it is apparent that excellent photographic properties are obtained and yellow color images having a good fastness to light are formed in Sample K in which the compound according to the present invention is used for dispersion of the yellow coupler. Similar results were obtained when Compounds (6), (7), (9) and (19) according to the present invention were used in place of Compound (2), respectively.

EXAMPLE 6

10 g of a DRR compound having the following formula (V):

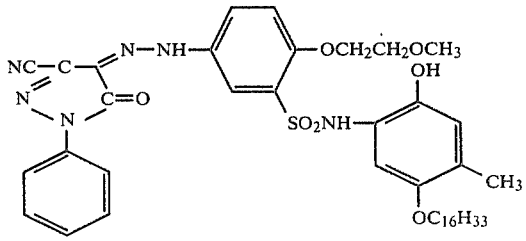

was dissolved in a solvent mixture of 5 g of Compound (2) according to the present invention and 15 ml of ethyl acetate at 70° C. The solution was added to a solution containing 100 ml of a 10% aqueous gelatin solution and 10 ml of a 5% aqueous sodium dodecylbenzene sulfonate and a mixture was stirred at 40° C. using a mixer to prepare a dispersion. This dispersion was a finely dispersed and stable dispersion.

On a polyethylene terephthalate transparent support were coated the layers described below in the order listed to prepare a light-sensitive sheet.

(1) Mordanting layer containing 3.0 g/m² of a mordant shown below:

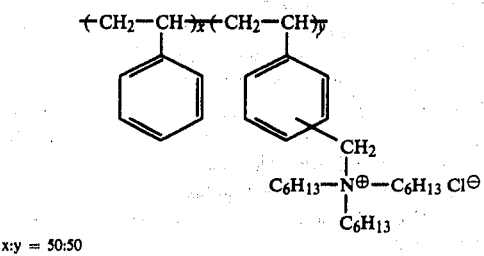

x:y = 50:50 and 3.0 g/m² of gelatin.

(2) White light reflective layer containing 20 g/m² of titanium oxide and 2.0 g/m² of gelatin.
(3) Light-shielding layer containing 2.70 g/m² of carbon black and 2.70 g/m² of gelatin.
(4) Layer formed by coating the above-described dispersion in an amount of 0.92 g/m² of the DRR compound.
(5) Layer containing an internal latent image type direct positive silver iodobromide emulsion (halogen composition in the silver halide: 1 mol % of iodide; silver amount: 1.5 g/m²; gelatin: 1.0 g/m²), 0.028 mg/m² of a fogging agent represented by the following formula:

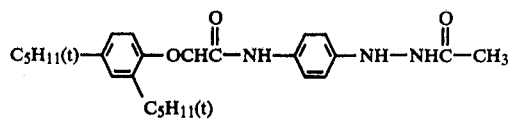

and 0.13 g/m² of sodium dodecylhydroquinone sulfonate.

(6) Layer containing 0.94 g/m² of gelatin.

Also, the processing solution and cover sheet shown below were prepared.

| Processing Solution: | |
|---|---|
| 1-Phenyl-4-methyl-4-hydroxymethyl-3-pyrazolidinone | 10 g |
| Methylhydroquinone | 0.18 g |
| 5-Methylbenzotriazole | 4.0 g |
| Sodium Sulfite (anhydrous) | 1.0 g |
| Carboxymethyl Cellulose Na Salt | 40.0 g |
| Carbon Black | 150 g |
| Potassium Hydroxide (28% aq. soln.) | 200 cc |
| H₂O | 550 cc |

The processing solution of the above composition was filled into a container rupturable with pressure by 0.8 g each.

Cover Sheet:

On a polyethylene terephthalate support were coated an acid polymer layer (neutralizing layer) containing 15 g/m² of polyacrylic acid (a 10 wt%aq. soln. having viscosity of about 1,000 cp) and a timing layer containing 3.8 g/m² of acetyl cellulose (hydrolysis of 100 g of acetyl cellulose forms 39.4 g of acetyl groups), and 0.2 g/m² of a styrenemaleic anhydride copolymer (composition ratio: styrene:maleic anhydride=about 60:40; molecular weight: about 50,000) to prepare a cover sheet.

Processing Step:

The above described cover sheet was superimposed on the above described light-sensitive sheet to form a film unit. Exposure was performed through a wedge having stepwise different density from the cover sheet side. Then, the processing solution described above was spread between both sheets in a thickness of 85 microns (the spreading was performed with assistance of a pressure roller). The processing was carried out at 25° C. After processing, the transferred images were observed through the transparent support for the light-sensitive sheet. The yellow transferred image formed one hour after the processing had a maximum density of 1.68, a minimum density of 0.31 and a good gradation.

While the invention has been described in detail and with reference to specific embodiments thereof, it will be apparent to one skilled in the art that various changes and modifications can be made therein without departing from the spirit and scope thereof.

What is claimed is:

1. In a silver halide photographic light-sensitive material comprising a support having thereon at least one silver halide emulsion layer and at least one hydrophilic organic colloid layer, said silver halide emulsion layer being the same as or different than said hydrophilic colloid layer and at least one of said silver halide emulsion layer or said hydrophilic organic colloid layer containing a dispersion of a substantially water-insoluble photographic additive dissolved in a solvent, the improvement wherein said solvent comprises a phosphoric acid ester represented by the following general formula (I):

 (I)

wherein R₁ represents a saturated alicyclic group; and R₂ and R₃, which may be the same or different, each represents a saturated alicyclic group, an alkyl group or an aryl group.

2. The silver halide photographic light-sensitive material of claim 1, wherein R₁ represents a saturated alicyclic group having 5 or more carbon atoms.

3. The silver halide photographic light-sensitive material of claim 2, wherein said saturated alicyclic group is substituted with an alkyl group, an aryl group, an alkoxy group, a cycloalkyl group, an alkoxyalkyl group, an acyloxy group or a halogen atom.

4. The silver halide photographic light-sensitive material of claim 1, wherein R₂ and R₃ each represents a saturated alicyclic group having 5 or more carbon atoms, an alkyl group having 1 to 30 carbon atoms or an aryl group having 6 to 24 carbon atoms.

5. The silver halide photographic light-sensitive material of claim 4, wherein said saturated alicyclic group is substituted with an alkyl group, an aryl group, an alkoxy group, a cycloalkyl group, an alkoxy alkyl group, an acyloxy group or a halogen atom.

6. The silver halide photographic light-sensitive material of claim 4, wherein said alkyl group is an alkyl group substituted with an alkoxy group, a halogen atom, an aryl group, an acyloxy group or an aryloxy group.

7. The silver halide photographic light-sensitive material of claim 4, wherein said aryl group is an aryl group substituted with an alkyl group, an alkoxy group or a halogen atom.

8. The silver halide photographic light-sensitive material of claims 2 or 4, wherein said saturated alicyclic group for $R_1$, $R_2$ or $R_3$ is a cyclohexyl group.

9. The silver halide photographic light-sensitive material of claim 1, wherein said substantially water-insoluble photographic additive is a photographic coupler, an antioxidant, a fade preventing agent, a hardener, an oil-soluble filter dye, an oil-soluble ultraviolet absorbing agent, a fluorescent brightening agent, a development inhibitor releasing compound, a developing agent, a diffusible dye releasing coupler, a diffusible dye releasing redox compound or a dye developing agent.

10. The silver halide photographic light-sensitive material of claim 9, wherein said substantially water-insoluble photographic additive is a photographic coupler, an ultraviolet absorbing agent, a fade preventing agent or a DRR compound.

11. The silver halide photographic light-sensitive material of claim 9, wherein said substantially water-insoluble photographic additive is a photographic coupler.

12. The silver halide photographic light-sensitive material of claim 1, wherein said phosphoric acid ester is present in an amount of 0.05 to 15 parts by weight per part by weight of said substantially water-insoluble photographic additive.

13. The silver halide photographic light-sensitive material of claim 1, wherein said substantially water-insoluble photographic additive is a photographic coupler and said dispersion of said photographic coupler in said phosphoric acid ester represented by the general formula (I) is present in a light-sensitive silver halide emulsion layer.

14. The silver halide photographic light-sensitive material of claim 1, wherein said hydrophilic organic colloid layer is a gelatin layer.

15. The silver halide photographic light-sensitive material of claim 1, wherein the total number of carbon atoms in $R_1$, $R_2$ and $R_3$ is about 12 to 50.

16. The silver halide photographic light-sensitive material of claim 1, wherein each of $R_1$, $R_2$ and $R_3$ represents a saturated alicyclic group.

17. The silver halide photographic light-sensitive material of claim 16, wherein said alicyclic group is alkyl substituted.

18. The silver halide photographic light-sensitive material of claim 16, wherein said alicyclic group is unsubstituted.

19. The silver halide photographic light-sensitive material of claim 18, wherein said alicyclic group is a cyclohexyl group.

* * * * *